US009554782B2

(12) United States Patent
Hadba et al.

(10) Patent No.: US 9,554,782 B2
(45) Date of Patent: Jan. 31, 2017

(54) MEDICAL DEVICES INCORPORATING FUNCTIONAL ADHESIVES

(71) Applicants: Covidien LP, Mansfield, MA (US); Sofradim Production, Trévoux (FR)

(72) Inventors: Ahmad Robert Hadba, Fort Worth, TX (US); Jack Kennedy, Guilford, CT (US); Sèbastien Ladet, Caluire & Cuire (FR)

(73) Assignees: Covidien LP, Mansfield, MA (US); Sofradim Production (FR)

( * ) Notice: Subject to any disclaimer, the term of this patent is extended or adjusted under 35 U.S.C. 154(b) by 134 days.

(21) Appl. No.: 14/309,930

(22) Filed: Jun. 20, 2014

(65) Prior Publication Data

US 2014/0303432 A1 Oct. 9, 2014

Related U.S. Application Data

(62) Division of application No. 13/070,782, filed on Mar. 24, 2011, now Pat. No. 8,795,331.

(60) Provisional application No. 61/317,450, filed on Mar. 25, 2010.

(51) Int. Cl.
| A61B 17/08 | (2006.01) |
| A61B 17/00 | (2006.01) |
| A61B 17/34 | (2006.01) |
| A61L 29/14 | (2006.01) |
| A61B 17/02 | (2006.01) |
| A61F 2/00 | (2006.01) |

(52) U.S. Cl.
CPC ..... *A61B 17/00491* (2013.01); *A61B 17/0218* (2013.01); *A61B 17/3421* (2013.01); *A61B 17/3423* (2013.01); *A61F 2/0063* (2013.01); *A61L 29/14* (2013.01); *A61B 2017/00495* (2013.01); *A61B 2017/00884* (2013.01); *A61B 2017/3419* (2013.01); *A61F 2002/0072* (2013.01)

(58) Field of Classification Search
CPC ............ A61B 17/00491; A61B 17/0218; A61B 17/3423; A61B 17/3421; A61B 2017/3419; A61B 2017/00495; A61B 2017/00884; A61F 2/0063; A61F 2002/0072; A61L 29/14
See application file for complete search history.

(56) References Cited

U.S. PATENT DOCUMENTS

| 3,767,085 A | 10/1973 | Cannon et al. |
| 4,326,532 A | 4/1982 | Hammar |
| 4,359,049 A | 11/1982 | Redl et al. |
| 4,464,321 A | 8/1984 | Pittalis et al. |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A | 10/1995 | Bastiaansen |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |

(Continued)

FOREIGN PATENT DOCUMENTS

| BE | 1008260 A6 | 2/1996 |
| EP | 0490854 A2 | 6/1992 |

(Continued)

OTHER PUBLICATIONS

The International Preliminary Report on Patentability and the Written Opinion of the International Searching Authority, corresponding toInternational Application No. PCT/IB2011/001116, dated Sep. 25, 2012.
Q. Shi, et al., "The Immobilization of Proteins on Biodegradable Polymer Fibers via Click Chemistry", Biomaterials, 29, (2008), pp. 1118-1126.
Jerome, et al., "Recent Advances in the Synthesis of Aliphatic Polyesters Ring-Opening Polymerization", Advanced Drug Delivery Reviews, 60, (2008), pp. 1056-1076.
Zhang, et al., "2-Azido-2-deoxycellulose: Synthesis and 1, 3-Dipolar Cycloaddition", Helvetica Chimica Acta, vol. 91, pp. 608-617 (2008).

(Continued)

*Primary Examiner* — Julian W Woo

(57) ABSTRACT

A method for treating a wound or defect at a surgical target site using a minimally invasive surgical procedure is provided which includes utilizing a surgical access device such as a port or a catheter having a plurality of reactive members of a specific binding pair releasably contained on a surface of the access device, the reactive members having affinity for binding a cellular component of tissue cells located at the target site; contacting the surface of the access device with the tissue cells, wherein upon contact of the reactive members on the surface of the access device with the tissue cells, the reactive members are released from the surface of the access device and bind to the tissue; providing a tissue repair member having secured thereto a plurality of complementary reactive members of the specific binding pair; and applying the tissue repair member to the tissue, wherein upon contact of the complementary reactive members on the surface of the tissue repair member with the reactive members on the tissue, covalent bonds are formed between the reactive members and the complementary reactive members, thus bonding the tissue repair member to the tissue. A surgical access device for use in minimally invasive surgery is provided which includes a plurality of reactive members of a specific binding pair releasably contained on a surface of the access device, the reactive members having an affinity for binding a cellular component of tissue cells and another affinity for binding complementary members of the specific binding pair.

23 Claims, No Drawings

(56) References Cited

U.S. PATENT DOCUMENTS

| | | |
|---|---|---|
| 5,804,318 A | 9/1998 | Pinchuk et al. |
| 5,830,539 A | 11/1998 | Yan et al. |
| 5,911,942 A | 6/1999 | Fofonoff et al. |
| 6,107,365 A | 8/2000 | Bertozzi et al. |
| 6,107,453 A | 8/2000 | Zuccato et al. |
| 6,123,667 A | 9/2000 | Poff et al. |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,605,107 B1 | 8/2003 | Klein |
| 6,624,245 B2 | 9/2003 | Wallace et al. |
| 6,774,278 B1 | 8/2004 | Ragheb et al. |
| 6,881,766 B2 | 4/2005 | Hain |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 8,617,206 B2 * | 12/2013 | Sargeant ............ A61B 17/0057 606/213 |
| 8,795,331 B2 | 8/2014 | Hadba et al. |
| 8,968,818 B2 * | 3/2015 | Belcheva ................ A61L 31/04 623/1.44 |
| 9,180,221 B2 * | 11/2015 | Sargeant ................ A61L 15/58 |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2006/0018948 A1 | 1/2006 | Guire et al. |
| 2006/0036022 A1 | 2/2006 | Callaghan et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0027603 A1 | 1/2009 | Samulski et al. |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0104589 A1 | 4/2010 | Govindan et al. |
| 2010/0121022 A1 | 5/2010 | Musa et al. |

(56) References Cited

U.S. PATENT DOCUMENTS

| | | |
|---|---|---|
| 2010/0159508 A1 | 6/2010 | Yang et al. |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |
| 2010/0303754 A1 | 12/2010 | Turpin et al. |
| 2011/0008251 A1 | 1/2011 | Chang et al. |
| 2011/0052696 A1 | 3/2011 | Hult et al. |
| 2011/0060107 A1 | 3/2011 | Matyjaszewski et al. |
| 2011/0143435 A1 | 6/2011 | Stayton et al. |
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 10/2008 |
| EP | 2014308 A2 | 1/2009 |
| EP | 2090592 A1 | 8/2009 |
| WO | 03028525 A2 | 4/2003 |
| WO | 2006012569 A1 | 2/2006 |
| WO | 2007041394 A2 | 4/2007 |
| WO | 2007121055 A1 | 10/2007 |
| WO | 2008013618 A1 | 1/2008 |
| WO | 2008075955 A2 | 6/2008 |
| WO | 2008077406 A2 | 7/2008 |
| WO | 2008108736 A1 | 9/2008 |
| WO | 2008115694 A2 | 9/2008 |
| WO | 2008120016 A1 | 10/2008 |
| WO | 2010095049 A1 | 8/2010 |

OTHER PUBLICATIONS

R. Riva, et al., "Contribution of "Click Chemistry" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (.epsilon.—caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-O-acetyl-1-thio-.beta.-D-glucopyranose to 4-deoxy-1,2-O-isopropylident-L-glycero-pent-4-enopyranos-3-ulose—a convenient route to novel4-deoxy-(1.fwdarw.5)-5-C-thiodisaccharides", Carbohydrate Research, 342, (2007), 1929-1933.

Marra, et al., "Validation of the Copper(I)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of .beta.-cyclodextrin with oligoethyleneamines", Biomaterials, 30, (2009), pp. 928-938.

Arora, et al., "A Novel Domino-click Approach for the Synthesis of Sugar Based Unsymmetrical bis-1,2,3-triazoles", Carbohydrate Research, 343, (2008), 139-144.

Chen, et al., "Synthesis of a C.sub.3-symmetric (1.fwdarw.6)-N-acetyl-.beta.-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, et al., "Effects of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via i to i + 4 Intramolecular Side-chain to Side-chain Azide-Alkyne 1,3-Dipolar Cycloaddition" J. Org. Chem., 2008, 73 (15), pp. 5663-5614.

Dijk, et al., "Synthesis of Peptide-Based Polymers by Microwave-Assisted Cycloaddition Backbone Polymerization," Biomacro molecules, 2007, 8(2), pp. 327-330.

Koster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

(56) References Cited

OTHER PUBLICATIONS

Krouit, et al., "Cellulose surface grafting with polycaprolactone by heterogeneous click-chemistry", European Polymer Journal 44, Dec. 2008, pp. 4074-4081.
Nandivada, et al. "Reactive polymer coatings that 'Click'.", Angewandte Chemie, International Edition 45, Apr. 2006, pp. 3360-3363.
Ossipov and Hilborn, Poly(vinyl alcohol)-Based Hydrogels Formed by "Click Chemistry", Macromelecules 2006, 39, pp. 1709-1718.
Binder and Sachsenhofer, "Click Chemistry in Polymer and Materials Science", Macromolecular Rapid Commun. 2007, 28, pp. 15-54.

\* cited by examiner

MEDICAL DEVICES INCORPORATING FUNCTIONAL ADHESIVES

CROSS-REFERENCE TO RELATED APPLICATIONS

This application is a divisional of U.S. patent application Ser. No. 13/070,782 filed Mar. 24, 2011, now U.S. Pat. No. 8,795,331, which claims benefit of U.S. Provisional Application No. 61/317,450 filed Mar. 25, 2010, and the disclosures of each of the above-identified applications are hereby incorporated by reference in their entirety.

BACKGROUND

1. Technical Field

The present disclosure relates to adhesive modalities for repair of biological tissues.

2. Related Art

Techniques for repairing damaged or diseased tissue are widespread in medicine. Minimally invasive procedures are continually increasing in number and variation. Forming a relatively small diameter temporary pathway to a surgical site is a key feature of most minimally invasive surgical procedures. A common method of providing such a pathway involves inserting a trocar assembly through the skin. Trocar assemblies typically include an obturator removably inserted through a cannula or port assembly. "Cannula" and "port" are used interchangeably herein. The obturator is assembled with the cannula portion such that the obturator's sharp tip portion extends from a distal end opening of the cannula to facilitate insertion of the cannula through the body wall of the patient. Placement of the cannula allows access to interiorly disposed surgical targets through the cannula. In this manner, specially designed tools are used to manipulate and repair tissue at such sites.

Wound closure devices such as sutures, staples and other repair devices such as mesh, plug or patch reinforcements are frequently used for repair and can be applied through a port. Surgical adhesives have been used to augment and, in some cases, replace sutures and staples in wound closure. For example, in the case of hernias, techniques involving the use of a mesh or patch to reinforce the abdominal wall are being used. Plugs may be used to seal the opening left from a port. The mesh, plug or patch can generally be held in place by suturing or stapling to the surrounding tissue. Unfortunately, the use of such sutures or staples may increase the patient's discomfort and, in certain instances, there may be a risk of weakening thin or delicate tissue where they are attached. Certain techniques involve placing a mesh, plug or patch against the repair site without suturing or stapling, e.g., allowing the pressure of the peritoneum to hold the patch against the posterior side of the abdominal wall. However, fixation of the mesh, plug or patch is generally preferred in order to avoid folding, shrinkage, and migration of the mesh or patch. Surgical adhesives such as cyanoacrylates and fibrin glues have been used as fixatives in lieu of, or in addition to, suturing or stapling the mesh, plug or patch. However, fibrin adhesives can be difficult to prepare and store. Cyanoacrylates may cause irritation at the point of application and may not provide a sufficient degree of elasticity. In addition, surgical adhesives can tend to form a physical barrier between the item or items being attached to biological tissue, thus interfering with tissue ingrowth into the item when ingrowth is desired.

Click chemistry is a popular term for reliable reactions that make it possible for certain chemical building blocks to "click" together and form an irreversible linkage. See, e.g., U.S. Pub. No. 2005/0222427. Since its recent introduction, click chemistry has been used for ligation in biological and medical technology. In the case of azide-alkyne click chemistry, the reactions may be catalyzed or uncatalyzed. For example, copper-free click chemistry was recently developed by Bertozzi and colleagues using difluorinated cyclooctyne or DIFO, that reacts with azides rapidly at physiological temperatures without the need for a toxic catalyst. See, e.g., Baskin et al., Copper Free Click Chemistry for Dynamic In Vivo Imaging, PNAS, vol. 104, no. 43, 16793-16797 (October 23, 2007). The critical reagent, a substituted cyclooctyne, possesses ring strain and electron-withdrawing fluorine substituents that together promote a [3+2] dipolar cycloaddition with azides. See also, U.S. Pub. No. 2006/0110782 and Codelli et al., Second Generation Difluorinated Cyclooctynes for Copper-Free Click Chemistry, J.Am.Chem.Soc., vol. 130, no. 34, 11486-11493 (2008). Another suitable cyclooctyne is 6,7-dimethoxyazacyclooct-4-yne (DIMAC). See, Sletton and Bertozzi, A hydrophilic azacyclooctyne for Cu-free click chemistry, Org. Lett. (2008) 10 (14), 3097-3099. Other click chemistry reactions include Diels-Alder reactions, thiol-alkene reactions, and maleimide-thiol reactions. There is a continuing need to generate improvements in tissue repair technology and advance the state of the art.

SUMMARY

A method for treating a wound or defect at a target site using a minimally invasive surgical procedure includes providing a surgical access device such as a port or a catheter having a plurality of reactive members of a specific binding pair releasably contained on a surface of the access device, the reactive members having affinity for binding a cellular component of tissue cells located at the target site; contacting the surface of the access device with the tissue cells, wherein upon contact of the reactive members on the surface of the access device with the tissue cells, the reactive members are released from the surface of the access device and bind to the tissue; providing a tissue repair member having secured thereto a plurality of complementary reactive members of the specific binding pair; and applying the tissue repair member to the tissue, wherein upon contact of the complementary reactive members on the surface of the tissue repair member with the reactive members on the tissue, covalent bonds are formed between the reactive members and the complementary reactive members, thus bonding the tissue repair member to the tissue.

A surgical access device for use in minimally invasive surgery is provided which includes a coating having a plurality of reactive members of a specific binding pair releasably contained on a surface of the access device, the reactive members having an affinity for binding a cellular component of tissue cells and another affinity for binding complementary members of the specific binding pair.

A kit is provided which includes a surgical access device having a plurality of reactive members of a specific binding pair for binding to complementary reactive members of the specific binding pair, said reactive members releasably contained on a surface of the access device, a tissue repair member such as a matrix, scaffold, plug, mesh or patch which has a plurality of the complementary reactive members of the specific binding pair attached to a surface of the tissue repair member and a container which houses the surgical access device and tissue repair member.

DETAILED DESCRIPTION

Efficient and effective repair of interiorly disposed wounds or defects in a patient such as those which may occur in hollow organs and/or port sites used in connection with minimally invasive surgery is provided by a surgical bonding system that covalently bonds a tissue repair member to tissue at the site of the wound or defect (collectively "the target site"). Minimally invasive surgery at a target site utilizing an access device such as a port or catheter having a rapidly disintegrating coating on its surface provides release of reactive members of a specific binding pair to the target site. The reactive members are designed to have an affinity for one or more cellular components of tissue cells located at the target site which causes the reactive members to bind securely to the tissue cells. A tissue repair member is securely provided with complementary reactive members of the specific binding pair which covalently bond to the reactive members of the specific binding pair, thus causing adhesion of the tissue repair member to tissue cells at the target site. In this manner, a wound or defect of the tissue may be covered and/or closed by the tissue repair member. Techniques, tools and compositions herein are useful in a variety of surgical repair procedures such as closing defects in hollow organs, e.g., the gastrointestinal tract, lumens such as blood vessels and/or port sites.

The surgical bonding system herein covalently bonds reactive members and complementary reactive members of a specific binding pair to one another via click chemistry. Click chemistry refers to a collection of reactive members having a high chemical potential energy capable of producing highly selective, high yield reactions. The reactive members and complementary reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitrile oxides, azides, and diazoalkanes. Metal catalyzed click chemistry is an extremely efficient variant of the Huisgen 1,3-dipolar cycloaddition reaction between alkyl-aryl-sulfonyl azides, C-N triple bonds and C-C triple bonds which is well-suited herein. The results of these reactions are 1,2 oxazoles, 1,2,3 triazoles or tetrazoles. For example, 1,2,3-triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

a)

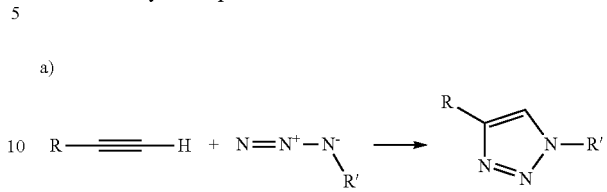

where R and R' are a polymeric material or a component of a biologic tissue.

The Diels-Alder reaction combines a diene (a molecule with two alternating double bonds) and a dienophile (an alkene) to make rings and bicyclic compounds. Examples include:

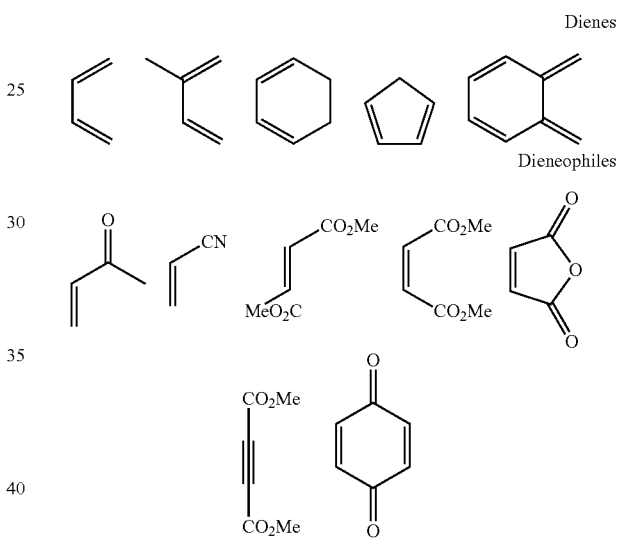

The thiol-alkene (thiol-ene) reaction is a hydrothiolation, i.e., addition of RS-H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of conventional initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

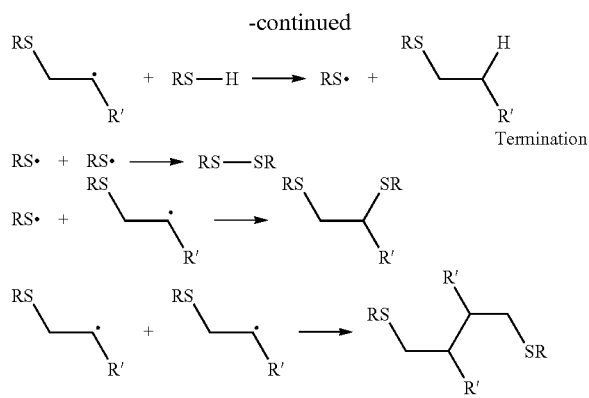
Termination

In accordance with the disclosure herein, an access device such as a port or a catheter for use in minimally invasive surgery is provided with a surface coating containing and/or overlaying a plurality of reactive members of a specific binding pair. The surface coating preferably provides relatively quick release of the reactive members to surrounding tissue at the target site to insure release of the reactive members while the access device is deployed in the patient. Release of the reactive members may occur, e.g., from about 0.05 minutes to about 60 minutes after placement of the access device in proximity to the target site. Coatings which provide rapid release of agents contained by the coating are well known to those skilled in the art as are techniques for applying such coatings, e.g., dip coating, spray coating, vapor deposition and the like.

The reactive members may be applied directly to the access device by, e.g., spraying, dipping, painting and vapor deposition and then coated with a disintegrable surface coating. Alternatively, the reactive members may be intermixed with a disintegrable coating which is applied to the surface of the access device. Indeed, the reactive members may be applied directly to the access device and, in addition, intermixed with a disintegrable coating which is applied over the initial coating of reactive members to the surface of the access device.

When the access device is inserted into a patient, the coating disintegrates by dissolving or otherwise degrading, thereby releasing the reactive members to surrounding tissue at the target site. As described below, the reactive members are provided with moieties having affinity to cellular components of tissue cells at the target site. Suitable coating materials include, e.g., pharmaceutically acceptable, water soluble, inert compounds or polymers used for film-coating applications such as sugar, dextrans, poly(ethylene glycol), polyvinylpyrrollidone, poly(vinyl alcohol), carboxymethyl cellulose, oxidized cellulose, hydroxypropyl cellulose, hydroxymethyl cellulose, hydroxypropyl methylcellulose, chitosan, alginate, collagen, gelatin and the like and combinations thereof.

In accordance with the disclosure herein, a tissue repair member, such as a surgical patch, scaffold, matrix, plug or mesh, is provided with a plurality of complementary reactive members of a specific binding pair attached to the surface of the tissue repair member. When the complementary reactive members of the tissue repair member are contacted with biological tissue containing reactive members of the specific binding pair, covalent attachment occurs, thus adhering the tissue repair member to the tissue. In embodiments, the reactive members may be either a dipolarophile or a 1,3 dipolar compound depending on which complement is applied to the target tissue or the tissue repair member. For example, if a dipolarphile is located on the tissue repair member, the 1,3 dipolar compound will be located on the tissue. If a dipolarphile is located on the tissue, the 1,3 dipolar compound will be located on the tissue repair member. In embodiments, the Diels-Alder members of a specific binding pair may be either a diene and a dienophile depending on which complement is applied to the target tissue or the tissue repair member. For example, if a diene is located on the tissue repair member, the dienophile can be located on the tissue. If a diene is located on the tissue, the dienophile can be located on the tissue repair member. In embodiments, the thiol-ene members of a specific binding pair may be either a thiol and an alkene depending on which complement is applied to the target tissue or the tissue repair member. For example, if a thiol is located on the tissue repair member, the alkene can be located on the tissue. If a thiol is located on the tissue, the alkene can be located on the tissue repair member.

The tissue repair member may be constructed from biocompatible absorbable polymers or biocompatible non-absorbable polymers. Examples of suitable polymers include polycarbonates, polyolefins, polymethacrylates, polystyrenes, polyamides, polyurethanes, polyesters, poly(ethylene terephthalate), poly(lactic acid), poly(glycolic acid), polycaprolactone, poly(hydroxbutyrate), polydioxanones (e.g., 1,4-dioxanone), polymers of δ-valerolactone, dioxepanones (e.g., 1,4-dioxepan-2-one and 1,5-dioxepan-2-one), poly (phosphazine), poly(ethylene glycol), poly(ethylene oxides), polyacrylamides, cellulose esters, fluoropolymers, vinyl polymers, silk, collagen, alginate, chitin, chitosan, hyaluronic acid, chondroitin sulfate, glycosaminoglycans, poly(hydroxyethyl methacrylate), polyvinylpyrrolidone, poly(vinyl alcohol), poly(acrylic acid), polyacetate, polypropylene, glycerols, poly(amino acids), copoly(ether-esters), polyalkylene oxalates, polyamides, poly(iminocarbonates), poly(alkylene oxalates), polyoxaesters, polyorthoesters, polyphosphazenes, polypeptides and copolymers, block copolymers, homoploymers, blends and combinations thereof.

In the present application, the term "bioresorbable" and "bioabsorbable" are used interchangeably and are intended to mean the characteristic according to which an implant and/or a material is resorbed by the biological tissues and the surrounding fluids and disappears in vivo after a given period of time, that may vary, for example, from one day to several months, depending on the chemical nature of the implant and/or of the material. Non bioresorbable material—also called permanent material—is not substantially resorbed by tissues and surrounding fluids, after 2 years and more, keeping in particular most (e.g., >80%) of their mechanical properties after such a time. The term "biocompatible" is intended to mean the characteristic according to which an implant and/or a material is well integrated by the biological tissues and the surrounding fluids without inducing excessive inflammation reaction around the bulk of the material or due to its degradation. The material should avoid also the formation of a fibrous capsule which usually results in the delay of the cellular integration of a porous implant.

Many of the above described examples of polymers do not contain functional groups in their molecules. In embodiments, the complementary reactive members are attached to the tissue repair member by surface modification techniques such as plasma treatment, silane coupling treatment and acid sensitization. Surface activation of the tissue repair member can be achieved by acid or base hydrolysis, treatment by means of cold plasma, by chemical reactions or electromagnetic radiations.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, $Ba(OH)_2$, $Mg(OH)_2$, NaOH, KOH, $Na_2CO_3$, $Ca(OH)_2$ and the weak bases, such as for example $NH_4OH$ and the amines such as methylamine, ethylamine, diethylamine and dimethylamine. Acids suitable for surface hydrolysis treatments can be chosen, for example, from among HCl, $HClO_3$, $HClO_4$, $H_2SO_3$, $H_2SO_4$, $H_3PO_3$, $H_3PO_4$, HI, $HIO_3$, HBr, lactic acid, glycolic acid. Surface activation by means of hydrolysis can be conducted at temperatures preferably comprised between 0 degrees Celsius and the material softening temperature.

Plasma treatment can be carried out both in the presence of a gas, for example air, Ar, $O_2$ with the formation of surface activation of oxygenate type, such as —OH, —CHO, —COOH.

Surface treatment, whether hydrolytic or with plasma, can remain unaltered or can be followed by further chemical modifications to provide the first reactive groups on the bioabsorbable polymeric substrate. Thus, for example, the COONa groups generated by a base hydrolysis can be subsequently converted into COOH groups by treatment with strong mineral acids. Further, the surface freeing of alcoholic groups by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—CH2—CH2—COOH groups. Suitable surface activation techniques are disclosed in U.S. Pat. No. 6,107,453, the entire disclosure of which is incorporated herein by this reference.

During manufacture of polymers, pendant functional groups can be incorporated into the polymer backbone by, e.g., copolymerization with functionalized monomer such as lactones, cyclic carbonates and morpholine-2,5-diones. The azido group, $N_3$ is a nucleophilic group that will exchange with other nucleophilic groups, e.g., —OH, —$NH_2$ and halogens (Br, Cl, or I). For example, 1,3-dipolar compounds may be conjugated to aliphatic polyesters, by copolymerizing ε-caprolactone and α-chloro-ε-caprolactone and then substituting an azide group for the Cl atom. Polyesters can incorporate pendant dipolarophiles, e.g., propargyl groups, by copolymerization of ε-caprolactone and α-propargyl-δ-valerolactone. Copolymers of L-lactide containing propargyl groups may, e.g., be prepared by ring opening copolymerization of 5-methyl-5-propargyloxycarbonyl-1,3-dioxanone with L-lactide at a molar ratio of about 90:10 with $ZnEt_2$ as a catalyst. See, Shi et al., Biomaterials, 29 (2008) 1118-1126. Azide functionalized polystyrene is synthesized using atom transfer radical polymerization and subsequent modification with azidotrimethylsilane and tetrabutylammonium fluoride. See, Dirks, et al., Chem. Comm., (2005) 4172-4174. Azides may be incorporated onto methacrylates, e.g., 3-azidopropyl methacrylate which is copolymerized to a block copolymer. Diels-Alder functionalities and thiol-ene functionalities are likewise incorporated into polymers herein.

In embodiments, the tissue repair member is applied through the access device. In embodiments, the tissue repair member is a surgical patch. The surgical patch may be selected from any conventional patch type that is suitable for use in tissue reinforcement, e.g., hernia repair, or as an anti-adhesion barrier, hemostatic patch, scaffold, matrix, bandages, pledgets and the like. In embodiments, the tissue repair member is a plug such as an umbrella-like plug which can be applied through a port to seal, e.g., the peritoneal portion of an access site. In embodiments, the tissue repair member potentially guides tissue in-growth. For example, the tissue repair member may be porous, which allows in-growth of tissue. Many types of tissue repair members are currently available and are well known to those skilled in the art. Exemplary polymeric tissue repair member materials include nonabsorbable polyester cloth, polyester sheeting, acrylic cloth, polyvinyl sponge or foam, polytetrafluroethylene (PTFE), expanded PTFE, and polyvinyl cloth. Any of the biocompatible polymers listed above may be utilized. In embodiments, the tissue repair member is a surgical mesh, e.g., polypropylene mesh, nylon mesh, and Dacron mesh. Exemplary absorbable meshes include collagen, polyglycolic acid, polyglactin, polycaprolactone, chitosan, and carbon fiber mesh. It should be understood that any of the above-mentioned biocompatible polymers may be suitable for use herein.

Indeed, the tissue repair member may be produced from fibers or sheets of any biocompatible polymer using any techniques known to those skilled in the art, such as knitting, weaving, tatting, nonwoven techniques, freeze drying, solvent casting and the like. It is envisioned that the tissue repair member may be formed from any permanent biocompatible materials (e.g. polyesters, polypropylene), biodegradable biocompatible materials (e.g. pol(ylactic acid), poly(glycolic acid), oxidized cellulose, and chitosan) or with a combination at any proportion of both permanent and biodegradable materials. The tissue repair member may, for example, have an openwork three-dimensional ("3D") structure (see, e.g. U.S. Pat. No. 6,451,032, the entire disclosure of which is incorporated herein by reference), e.g., a "honeycomb" structure, and thus a certain thickness which separates the two surfaces of the fabric.

In certain embodiments, the tissue repair member is composed of a biopolymer foam having openings or pores over at least a portion of a surface thereof. The pores may be in sufficient number and size so as to interconnect across the entire thickness of the porous layer. Alternatively, the pores may not interconnect across the entire thickness of the porous layer. Closed cell foams are illustrative examples of structures in which the pores may not interconnect across the entire thickness of the porous layer. In yet other embodiments, the pores do not extend across the entire thickness of the foam, but rather are present at a portion of the surface thereof. In some embodiments, the openings or pores are located on a portion of the surface of the porous layer, with other portions of the porous layer having a non-porous texture. Those skilled in the art may envision other pore distribution patterns and configurations for the foam. In embodiments, rapidly degrading or dissolving particles distributed in the tissue repair member may be utilized to create porosity.

In certain embodiments, the foam may be made from non-denatured collagen or collagen which has at least partially lost its helical structure through heating or any other known method, consisting mainly of non-hydrolyzed chains, and having a molecular weight, in embodiments, of about 100 kDa. The collagen used for the porous layer of the present disclosure may be native collagen or atelocollagen, which may be obtained via pepsin digestion and/or after moderate heating as defined hereinabove. The origin and type of collagen may be as indicated for the non-porous layer described hereinabove.

The collagen may be cured to any desired degree. The collagen suspension or solution may be made from non-cured, moderately cured, highly cured or extremely highly cured collagens or combinations thereof at any proportions. As used herein, the term "moderately cured" is intended to mean that the degradation of the porous layer will be at least about 90% complete (as measured by residual weight) by the end of about three weeks of implantation; the term "highly cured" is intended to mean that the degradation of the porous layer will be at least about 90% complete (as measured by residual weight) by the end of about three months of implantation; and the term "extremely highly cured" is intended to mean that the degradation of the porous layer will be at least about 90% complete (as measured by residual weight) by the end of about two years of implantation.

Moderately cured collagen may be obtained by oxidative cleavage of collagen by periodic acid or one of its salts, as described for collagens of the non-porous layer. In embodiments, highly cured collagen may be made from collagen cross-linked by glutaratdehyde or by any other known cross-linking agents such as, for example, but not limited to, isocyanates, n-hydroxysuccinimidal ester containing molecules, carbodiimides, Genipin, and the like. The degree of crosslinking distinguishes between highly cured and very highly cured materials. Techniques for curing to various degrees are within the purview of those skilled in the art.

In embodiments, the collagen may optionally include non-collagenic components, such as glycosaminoglycans, for example, but not limited to, chitosan, heparin, hyaloronic acid, and the like. The glycosaminoglycans, in embodiments, display a degree of acetylation (DA) of from about 0.5% to about 50%, have a molecular weight ranging from about 100 g/mol to about 1,000,000 g/mol, and may display a low polydispersity index of from about 1 to about 2. In certain embodiments, the collagen may be a mixture of chitosans and other glycosamoniglycans, for example, but not limited to, hyaluronic acid, which, after deacettylation have free amino groups capable of cross-linking to the oxidized collagen. It is contemplated that the collagen suspension or solution may be a combination of oxidized collagen and chitosan which can form a cross-linked network.

In embodiments, the tissue repair member may be formed from one or more bioresorbable, natural biological polymers. Suitable natural biological polymers include, but are not limited to, collagen, gelatin, cellulose, hydroxypropyl cellulose, carboxymethyl cellulose, chitin, chitosan, hyaluronic acid, chondroitin sulfate and other gycosaminoglycans and combinations thereof. In embodiments, the polymer constituent may be a polysaccharide such as chitin or chitosan, or polysaccharides modified by oxidation of alcohol functions into carboxylic functions such as oxidized cellulose. It is contemplated that the natural biological polymers may be combined with any biocompatible synthetic materials to produce the porous layer of the tissue repair member.

In embodiments, the tissue repair member may incorporate a medicinal agent. The term "medicinal agent", as used herein, is meant to be interpreted broadly and includes any substance or mixture of substances which may have any clinical use in medicine. Thus, medicinal agents include drugs, enzymes, proteins, peptides, glycoproteins, or diagnostic agents such as releasable dyes which may have no biological activity per se. Examples of classes of medicinal agents that can be used include antimicrobials, analgesics, antipyretics, anesthetics, antiepileptics, antihistamines, anti-inflammatory agents, anti-clotting agents, cardiovascular drugs, diagnostic agents, sympathomimetics, cholinomimetics, anti-muscarinics, antispasmodics, hormones, growth factors, muscle relaxants, adrenergic neuron blocks, antineoplastics, immuno suppressants, gastrointestinal drugs, diuretics, steroids and enzymes. It is also intended that combinations of medicinal agents can be used. Those skilled in the art are familiar with various techniques for incorporating a medicinal agent into a coating to allow rapid or sustained release of the medicinal agent.

Biological tissue is provided with reactive members of a specific binding pair by conjugation to various cellular components of tissue such as proteins, lipids, oligosaccharides, oligonucleotides, glycans, including glycosaminoglycans. In embodiments, the reactive members are attached directly to cellular components of the tissue. In embodiments, the reactive members are attached to cellular components of the tissue via a linker. In either case, situating the reactive members on the tissue is accomplished by contacting the access device with the tissue, allowing the coating to disintegrate thereby contacting the reactive members with the target tissue and its cellular components such that the reactive member binds to preselected cellular components.

1,3-Dipolar compounds can be incorporated into proteins, lipids, oligosaccharides, oligonucleotides and glycans using, e.g., metabolic machinery, covalent inhibitors and enzymatic transfers. For example, an azido group, $N_3$, can be applied at the N-terminus of proteins or peptides using azidoacetyl chloride. See, e.g., Haridas, et al., Tetrahedron Letters 48 (2007) 4719-4722. $NaN_3$ is an azidizing agent which is capable of aziding proteins by simply contacting the proteins with a 10 times molar excess of $NaN_3$. A process for C-terminal azidization is described in Cazalis, et al., Bioconjugate Chem., 15 (2004) 1005-1009. Incubation of cells with peracetylated N-azidoacetylmannosamine provides cell surface glycans with azido sialic acid. See, e.g., Codelli et al., J. Amer. Chem. Soc., 130 (34) 11486-11493 (2008). Azido-tagged lipids are described in Smith, et al., Bioconjugate Chem., 19 (9), 1855-1863 (2008). PEGylation is a commonly used technique for adding groups to peptides and proteins and is suitable for use herein. For example, PEG may be covalently bound to amino acid residues via a reactive group. Reactive groups (as opposed to reactive members herein) are those to which an activated PEG molecule may be bound (e. g., a free amino or carboxyl group). For example, N-terminal amino acid residues and lysine (K) residues have a free amino group and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein. Those skilled in the art can utilize any known process for coupling a 1,3-dipolar compound into proteins, lipids, oligosaccharides, oligonucleotides and glycans.

Dipolarophile functionalized proteins and peptides can be synthesized by linking at the N-terminus with, for example, an alkyne (e.g., 3 butynyl chloroformate), in connection with a tripeptide (GlyGlyArg). See, Dirks, et al., supra. A suitable tripeptide herein is the well-known cell adhesion sequence RGD. It should be understood that, as used herein, "proteins" is intended to encompass peptides and polypeptides. In one embodiment, thiols on cysteines are functionalized with alkyne bearing maleimide. Id. Providing a C-terminal dipolarophile can be accomplished, e.g., by coupling with propargylamine using a cross-linking agent such as N-hydroxysuccinimide/DCC. See, e.g., Haridas, et al. supra. Terminal alkynes can be installed using metabolic building blocks such as alkynoic acids. Lipids may be functionalized with alkynes. For example, alkyne modified fatty acids can be generated by reaction of terminal alkynyl-alkyl bromide with trimethyl phosphine to yield a 16 carbon alkynyl-dimethylphosphonate. See, e.g., Raghavan et al., Bioorg. Med. Chem. Lett., 18 (2008) 5982-5986. As above, PEGylation may be used for adding dipolarophile groups to to peptides and proteins and is suitable for use herein. Diels-Alder functionalities and thiol-ene functionalities are likewise attached to proteins, lipids, oligosaccharides, oligonucleotides and glycans.

The reactive members may be also attached to biological tissue via a linker. In certain embodiments, the linker is or includes a ligand which bears a reactive member. The ligand binds to a desired target on the tissue and thus provides a vehicle for transporting and indirectly binding the reactive member to the tissue. The ligand herein is any molecule or combination of molecules which demonstrates an affinity for a target. Examples of ligands include nucleic acid probes, antibodies, biotin-avidin or streptavidin complexes, hapten conjugates, and cell adhesion peptides such as RGD. The mechanisms involved in obtaining and using such ligands are well-known. In embodiments, reactive members or complementary reactive members are incorporated into saccharides or polysaccharides and metabolically incorporated into cells. See, e.g., Baskin et al., supra.

Antibodies that specifically recognize antigens are useful in accordance with one embodiment herein. Antibodies which are conjugated to a reactive member are utilized to bind to proteins located on tissue. Monoclonal or polyclonal antibodies are raised against an antigen which can be any component of biological tissue and then purified using conventional techniques. The term "antibody" is intended to include whole antibodies, e.g., of any isotype (IgG, IgA, IgM, IgE, etc.), and to include fragments thereof which are also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The present disclosure includes polyclonal, monoclonal or other purified preparations of antibodies and recombinant antibodies.

After purification, the ligands (e.g., antibodies, nucleic acid probes, hapten conjugates and cell adhesion peptides), are conjugated or linked to reactive members or complementary reactive members in the manners described above. In addition, reactive members can be linked to ligands by cross-linking procedures which, in accordance with the present invention, do not cause denaturing or misfolding of the ligands. The terms "linked" or "conjugated" as used herein are used interchangeably and are intended to include any or all of the mechanisms known in the art for coupling the reactive members to the ligand. For example, any chemical or enzymatic linkage known to those with skill in the art is contemplated including those which result from photoactivation and the like. Homofunctional and heterobifunctional cross linkers are all suitable. Reactive groups (distinguishable from reactive members or complementary reactive members herein) which can be cross-linked with a cross-linker include primary amines, sulfhydryls, carbonyls, carbohydrates and carboxylic acids.

Cross-linkers are conventionally available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NHS-ester cross-linkers include disuccinimidyl glutamate, disucciniminidyl suberate and bis(sulfosuccinimidyl) suberate. Accessible amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines should be conducted at a pH of between about 7 and about 9 and a temperature between about 4° C. and 30° C. for about 30 minutes to about 2 hours. The concentration of NHS-ester cross-linker can vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl reactive cross-linkers include maleimides, alkyl halides, aryl halides and a-haloacyls which react with sulfhydryls to form thiol ether bonds and pyridyl disulfides which react with sulfhydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-{N-maleimido-methyl) cyclohexane-1-carboxylate and m-maleimidobenzoyl-N-hydroxysuccinimide ester. Examples of haloacetal cross-linkers include N-succinimidyl (4-iodoacetal) aminobenzoate and sulfosuccinimidyl (4-iodoacetal) aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodimides which result in formation of amide or hydrazone bonds. In this manner, carboxy-termini of peptides or proteins can be linked. Examples of carbodiimide cross-linkers include 1-ethyl-3-(3-dimethylaminopropyl)-carbodiimide hydrochloride and N, N$^1$-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which arc amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide cross-linkers discussed above.

Attachment of complementary reactive members to the tissue repair member functionalizes the tissue repair member such that upon exposure to their corresponding reactive members which are situated on tissue, they are activated and form a covalent bond, thus adhering the tissue repair member to the tissue. In one embodiment, a linker between the product of the reactive members or complementary reactive members and the biological tissue is degradable by, e.g., hydrolysis or enzymatic action. In this manner, the tissue repair member can be removable after a period of time. The degradable linkage may be, e.g., chelates or chemically or enzymatically hydrolyzable or absorbable. Illustrative chemically hydrolyzable degradable linkages include polymers, copolymers and oligomers of glycolide, dl-lactide, 1-lactide, caprolactone, dioxanone, and trimethylene carbonate. Illustrative enzymatically hydrolyzable biodegradable linkages include peptidic linkages cleavable by metalloproteinases and collagenases. Additional illustrative degradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In certain embodiments, the degradable linkage may contain ester linkages. Some non-limiting examples include esters of succinic acid, glutaric acid, propionic acid, adipic acid, or amino acids, as well as carboxymethyl esters.

The tissue repair member may be cut or otherwise formed to a desired shape, packaged in single or dual pouches and sterilized by gamma or beta irradiation at 25-35 KGy or by ethylene oxide. The ligand solution could be sterilized by the previous cited method or by filtration in sterile conditions on 0.22 µm filter.

A kit for use in minimally invasive surgery herein includes a surgical access device such as a port or a catheter coated with a plurality of reactive members of a specific binding pair, a tissue repair member such as a matrix, scaffold, plug, mesh or a patch which has a plurality of complementary reactive members of a specific binding pair attached to a surface of the tissue repair member and a container which houses the access device and tissue repair member. The kit may optionally include an applicator for positioning the tissue repair member through the access device to the target site. In embodiments, the kit contains a generator of microwaves or ultraviolet radiation.

It should be understood that variations can be made to the above embodiments that are with the purview of ordinary skill in the art. For example, other click chemistry reactions are suitable for use herein, e.g., Staudinger reaction of phosphines with alkyl azides. It is contemplated that the above-described cross-linkers may be applied to polymers which make up the tissue repair member to bind complementary reactive members thereto. Accordingly, those skilled in the art can envision modifications which are included within the scope of the claimed invention that are not expressly set forth herein.

What is claimed is:

1. A method for treating a wound or defect at a target site using a minimally invasive surgical procedure comprising:
   providing a surgical access device having a plurality of reactive members of a specific binding pair releasably contained on an exterior surface of the access device, the reactive members having affinity for binding a cellular component of tissue cells located at the target site;
   contacting the exterior surface of the access device with the tissue cells, wherein upon contact of the reactive members on the surface of the access device with the tissue cells, the reactive members are released from the exterior surface of the access device and bind to the tissue cells;
   providing a tissue repair member having secured thereto a plurality of complementary reactive members of the specific binding pair; and
   applying the tissue repair member to the tissue cells, wherein upon contact of the complementary reactive members on the surface of the tissue repair member with the reactive members on the tissue cells, covalent bonds are formed between the reactive members and the complementary reactive members, thus bonding the tissue repair member to the target site.

2. The method for treating a wound or defect at a target site using a minimally invasive surgical procedure according to claim 1 wherein the reactive members and the complementary reactive members of the specific binding pair bind to one another via a reaction selected from the group consisting of Huisgen cycloaddition reaction, a Diels-Alder reaction and a thiol-ene reaction.

3. The method for treating a wound or defect at a target site using a minimally invasive surgical procedure according to claim 2 wherein the reactive and the complementary reactive members of the specific binding pair are alkynes and azides.

4. The method for treating a wound or defect at a target site using a minimally invasive surgical procedure according to claim 3 wherein the reactive members are alkynes and the complementary reactive members are azides.

5. The method for treating a wound or defect at a target site using a minimally invasive surgical procedure according to claim 4 wherein the reactive and complementary reactive members of the specific binding pair are dienes and alkenes.

6. The method for treating a wound or defect at a target site using a minimally invasive surgical procedure according to claim 3 wherein the reactive members are azides and the complementary reactive members are alkynes.

7. The method for treating a wound or defect at a target site using a minimally invasive surgical procedure according to claim 2 wherein the reaction is catalyzed by copper to activate an alkyne and an azide for [3+2] cycloaddition.

8. The method for treating a wound or defect at a target site using a minimally invasive surgical procedure according to claim 2 wherein the reaction involves a cyclooctyne reagent and an azide for [3+2] cycloaddition.

9. The method for treating a wound or defect at a target site using a minimally invasive surgical procedure according to claim 2 wherein the reactive and complementary reactive members of the specific binding pair are thiols and alkenes.

10. The method for treating a wound or defect at a target site using a minimally invasive surgical procedure according to claim 2 wherein the complementary reactive members of the specific binding pair are secured to the tissue repair member by surface modification techniques selected from the group consisting of plasma treatment, silane coupling treatment and acid sensitization.

11. The method for treating a wound or defect at a target site using a minimally invasive surgical procedure according to claim 1 wherein a rapidly disintegrating coating on the exterior surface of the access device causes release of the reactive members of a specific binding pair.

12. The method for treating a wound or defect at a target site using a minimally invasive surgical procedure according to claim 11 wherein the rapidly disintegrating coating is made from a compound selected from the group consisting of sugar, poly(ethylene glycol), polyvinylpyrrolidone, poly(vinyl alcohol), hydroxypropyl cellulose, hydroxymethyl cellulose, hydroxypropyl methylcellulose, gelatin and combinations thereof.

13. The method for treating a wound or defect at a target site using a minimally invasive surgical procedure according to claim 1 wherein the surgical access device is a port or catheter.

14. The method for treating a wound or defect at a target site using a minimally invasive surgical procedure according to claim 1 wherein the reactive members are conjugated to a linker adapted to link the reactive members to the tissue cells.

15. The method for treating a wound or defect at a target site using a minimally invasive surgical procedure to claim 14 wherein the reactive members bind to the tissue cells via an RGD linker.

16. The method for treating a wound or defect at a target site using a minimally invasive surgical procedure according to claim 14 wherein the reactive members bind to the tissue cells via a ligand-receptor linkage.

17. The method for treating a wound or defect at a target site using a minimally invasive surgical procedure according to claim 16 wherein the ligand-receptor linkage is selected from the group consisting of antibody-antigen, biotin-avidin and biotin-streptavidin.

18. The method for treating a wound or defect at a target site using a minimally invasive surgical procedure according to claim 17 wherein the reactive members are conjugated to a linker selected from the group consisting of antibody, Fab, F(ab')2, Fv, single chain antibody (SCA) and single complementary-determining region (CDR).

19. The method for treating a wound or defect at a target site using a minimally invasive surgical procedure according to claim 16 wherein the ligand binds to a receptor selected from the group consisting of peptides, oligosaccharides, oligonucleotides and lipids.

20. The method for treating a wound or defect at a target site using a minimally invasive surgical procedure according to claim 14 wherein the linker is degraded by hydrolysis or enzymatic action.

21. The method for treating a wound or defect at a target site using a minimally invasive surgical procedure according to claim 1 wherein the tissue repair member is a patch, scaffold, matrix, plug or mesh.

22. The method for treating a wound or defect at a target site using a minimally invasive surgical procedure according to claim 21 wherein the tissue repair member is made of foam, woven material and non-woven material.

23. The method for treating a wound or defect at a target site using a minimally invasive surgical procedure to claim 1 wherein the tissue repair member is made of a polymer selected from the group consisting of polycarbonates, polyolefins, polymethacrylates, polystyrenes, polyamides, polyurethanes, poly(ethylene terephthalate), poly(lactic acid), poly(glycolic acid), polyhydroxbutyrate, dioxanones (e.g., 1,4-dioxanone), [delta]-valerolactone, 1,dioxepanones (e.g., 1,4-dioxepan-2-one and 1,5-dioxepan-2-one), poly(phosphazine), polyesters, poly(ethylene glycol, polyethylene oxides), polyacrylamides, cellulose esters, fluoropolymers, vinyl polymers, silk, collagen, alginate, chitin, chitosan, hyaluronic acid, chondroitin sulfate, poly(hydroxyethyl methacrylate), polyvinylpyrrolidone, poly(vinyl alcohol), poly(acrylic acid), polyacetate, polycaprolactone, polypropylene, glycerols, poly(amino acids), copoly(ether-esters), poly(alkylene oxides), polyamides, poly(iminocarbonates), poly(alkylene oxalates), polyoxaesters, polyorthoesters, polyphosphazenes, polypeptides and copolymers, block copolymers, homopolymers, blends and combinations thereof.

* * * * *